(12) United States Patent
Schlueter

(10) Patent No.: US 8,119,830 B2
(45) Date of Patent: Feb. 21, 2012

(54) DUAL FUNCTION UV-ABSORBERS FOR OPHTHALMIC LENS MATERIALS

(75) Inventor: Douglas C. Schlueter, Azle, TX (US)

(73) Assignee: Novartis AG, Basel (CH)

( * ) Notice: Subject to any disclaimer, the term of this patent is extended or adjusted under 35 U.S.C. 154(b) by 138 days.

(21) Appl. No.: 12/722,185

(22) Filed: Mar. 11, 2010

(65) Prior Publication Data

US 2010/0168438 A1 Jul. 1, 2010

Related U.S. Application Data

(62) Division of application No. 12/125,403, filed on May 22, 2008, now Pat. No. 7,709,652, which is a division of application No. 11/539,748, filed on Oct. 9, 2006, now Pat. No. 7,396,942, which is a division of application No. 10/753,254, filed on Jan. 8, 2004, now Pat. No. 7,119,210.

(60) Provisional application No. 60/438,978, filed on Jan. 9, 2003.

(51) Int. Cl.
C07C 229/00 (2006.01)
C07C 35/08 (2006.01)

(52) U.S. Cl. .......... 560/155; 549/27; 564/270; 564/123; 568/822

(58) Field of Classification Search .................. 560/155; 549/27; 564/270, 123; 568/822
See application file for complete search history.

(56) References Cited

U.S. PATENT DOCUMENTS

| | | | |
|---|---|---|---|
| 4,304,895 A | 12/1981 | Loshaek | |
| 4,528,311 A | 7/1985 | Beard et al. | |
| 4,612,358 A | 9/1986 | Besecke et al. | |
| 4,716,234 A | 12/1987 | Dunks et al. | |
| 4,785,063 A | 11/1988 | Slongo et al. | |
| 4,929,250 A | 5/1990 | Hung et al. | |
| 4,963,160 A | 10/1990 | Hung et al. | |
| 5,047,556 A | 9/1991 | Kohler et al. | |
| 5,098,445 A | 3/1992 | Hung et al. | |
| 5,133,745 A | 7/1992 | Falcetta et al. | |
| 5,141,990 A | 8/1992 | McKoy et al. | |
| 5,147,902 A | 9/1992 | Ichikawa et al. | |
| 5,164,462 A | 11/1992 | Yang | |
| 5,189,084 A | 2/1993 | Birbaum et al. | |
| 5,194,544 A | 3/1993 | Goldberg et al. | |
| 5,290,892 A | 3/1994 | Namdaran et al. | |
| 5,298,033 A | 3/1994 | Hung et al. | |
| 5,331,073 A | 7/1994 | Weinschenk, III et al. | |
| 5,384,235 A | 1/1995 | Chen et al. | |
| 5,399,692 A | 3/1995 | Hung et al. | |
| 5,500,024 A | 3/1996 | Hung et al. | |
| 5,648,488 A | 7/1997 | Stevenson | |
| 5,693,095 A | 12/1997 | Freemen et al. | |
| 5,837,792 A | 11/1998 | Meuwly et al. | |
| 5,869,588 A | 2/1999 | Toan et al. | |
| 5,914,355 A | 6/1999 | Kunzler et al. | |
| 5,928,629 A | 7/1999 | Allard et al. | |
| 5,928,630 A | 7/1999 | Richard et al. | |
| 5,942,564 A | 8/1999 | Kaschig et al. | |
| 5,945,465 A | 8/1999 | Ozark et al. | |

FOREIGN PATENT DOCUMENTS

| | | |
|---|---|---|
| EP | 0221630 A2 | 5/1987 |
| EP | 0343996 A2 | 11/1989 |
| EP | 0283166 B1 | 1/1992 |
| EP | 0693483 A1 | 1/1996 |
| EP | 0952467 A1 | 10/1999 |
| EP | 0582664 B1 | 10/2000 |
| WO | WO9850371 | 11/1998 |
| WO | WO9953348 | 10/1999 |
| WO | WO9958507 | 11/1999 |
| WO | WO9960428 | 11/1999 |
| WO | WO9963366 | 12/1999 |
| WO | WO0055212 | 9/2000 |
| WO | WO02078966 | 10/2002 |

OTHER PUBLICATIONS

Abu-Abdoun et. al., Journal of Polymer Science, Polymer Chemistry Edition (1983), 21 (11), pp. 3129-3144; abstract only.*
William Dickstein, et al., "Functional Polymers. XXVI. Co- and Terpolymers Involving Methacrylates N-Vinylpyrollidone, and Polymerizable Ultraviolet Stabilizers and Antioxidants," J. Macromol. Sci.-Chem., 1985, pp. 387-402, A22(4).
Jacqueline H. De Groot, et al., "Hydrophilic Polymeric Acylphospine Oxide Photoinitiators/Crosslinkers for in Vivo Blue-Light Photopolymerization," Biomacromolecules, 2001, pp. 1271-1278, vol. 2.
Jurgen Keck, et al., Deactivation Processes of 2-Hydroxyphenyl-1,3-5Triazines- Polymeric and Monomeric UV Absorbers of the Benzotriazole and Triazine Class, Die Angewandte Makromolekulare Chemie1997, pp. 119-138, vol. 252.
S. Knaus, et al., "Photoinitiators With Functional Groups. III. Water-Soluble Photoinitiators Containing Carbohydrate Residues," Journal of Polymer Science, Part A: Polymer Chemistry, 1995, pp. 929-939, vol. 33.
Jiang-Qing Pan, et al., "Synthesis and Characterization of New Monomers Containing UV-Absorber Function," Polymer Degradation and Stability, 1995, pp. 231-237, vol. 49.
J. F. Rabek, Photostabilization of Polymers, Chapter 1.1-1.3 (pp. 1-5) and Chapter 5.1-5.10 (pp. 202-249) and Chapter 7.3 (pp. 368-391), Elsevier Applied Science, London and New York, 1990.
Andrea Sustic, et al., "New 2(20hydroxyphenyl)2H-benzotriazole based polymer-bound unltraviolet stabilizers," ACS Polymer Prep., 1987, p. 226, vol. 28(2).

* cited by examiner

*Primary Examiner* — Elvis O Price
(74) *Attorney, Agent, or Firm* — Patrick M. Ryan

(57) ABSTRACT

Disclosed are UV absorbers that contain a labile functional group capable of initiating free radical polymerization.

6 Claims, No Drawings

DUAL FUNCTION UV-ABSORBERS FOR OPHTHALMIC LENS MATERIALS

This application is a divisional application of U.S. Ser. No. 12/125,403, filed May 22, 2008, which is a divisional application of U.S. Ser. No. 11/539,748, filed Oct. 9, 2006, now U.S. Pat. No. 7,396,942, which is a divisional application of U.S. Ser. No. 10/753,254, filed Jan. 8, 2004, now U.S. Pat. No. 7,119,210, which claims priority to U.S. Provisional Application, U.S. Ser. No. 60/438,978, filed Jan. 9, 2003.

FIELD OF THE INVENTION

This invention is directed to ophthalmic lens materials. In particular, this invention relates to ultraviolet light absorbers that also act as polymerization initiators for ophthalmic lens materials.

BACKGROUND OF THE INVENTION

Many UV light absorbers are known as ingredients for polymeric materials used to make ophthalmic lenses. UV absorbers are preferably covalently bound to the polymeric network of the lens material instead of simply physically entrapped in the material to prevent the absorber from migrating, phase separating or leaching out of the lens material. Such stability is particularly important for implantable ophthalmic lenses where the leaching of the UV absorber may present both toxicological issues and lead to the loss of UV blocking activity in the implant.

Numerous copolymerizable benzatriazole, benzophenone and triazine UV absorbers are known. Many of these UV absorbers contain conventional olefinic polymerizable groups, such as methacrylate, acrylate, methacrylamide, acrylamide or styrene groups. Copolymerization with other ingredients in the lens materials, typically with a radical initiator, incorporates the UV absorbers into the resulting polymer chain. Incorporation of additional functional groups, on a UV absorber may influence one or more of the UV absorber's UV absorbing properties, solubility or reactivity. If the UV absorber does not have sufficient solubility in the remainder of the ophthalmic lens material ingredients or polymeric lens material, the UV absorber may coalesce into domains that could interact with light and result in decreased optical clarity of the lens.

Examples of polymeric ophthalmic lens materials that incorporate UV absorbers can be found in U.S. Pat. Nos. 5,290,892; 5,331,073 and 5,693,095.

SUMMARY OF THE INVENTION

The present invention provides dual function UV absorbers. These UV absorbers contain a labile functional group capable of initiating radical to polymerization. These UV absorbers are suitable for use in ophthalmic lenses, including contact lenses, and are particularly useful in implantable lenses, such as intraocular lenses (IOLs).

Among other factors, the present invention is based on the finding that UV absorbers can be modified to incorporate a labile functional group capable of initiating polymerization of an olefinic ophthalmic lens material monomers without eliminating the UV absorber's UV absorbing activity, solubility or reactivity with ophthalmic lens material ingredients.

DETAILED DESCRIPTION OF THE INVENTION

Unless indicated otherwise, all ingredient amounts expressed in percentage terms are presented as % w/w.

The dual function UV absorbers ("DFUVAS") of the present invention contain a functional group that can initiate free radical polymerization. As such, these DFUVAS eliminate the need for two separate monomeric ingredients in the preparation of copolymeric ophthalmic lens materials. Instead of adding a conventional UV absorber to conventional ophthalmic lens-forming materials and separately adding a conventional polymerization initiator, a DFUVAS can be used in place these two conventional ingredients.

Many conventional thermal free radical initiators and many UV absorbers are known. The DFUVAS may be synthesized by reacting a UV absorber that contains a reactive functionality with a radical initiator while preserving the radical generating linkage. For example, 3-(2H-benzotriazol-2-yl)-4-hydroxyphenethyl alcohol (1) may be coupled to 4,4'-azobis(4-cyanopentanoic acid) (2) using a carbodiimide esterification agent. The product (3) can then initiate radical polymerization of a vinyl monomer (e.g., acrylate, methacrylate, acrylamide, methacrylamide, styrene) by application of heat and/or UV/visible light and the UV absorbing functionality will be to covalently attached to the polymer chain.

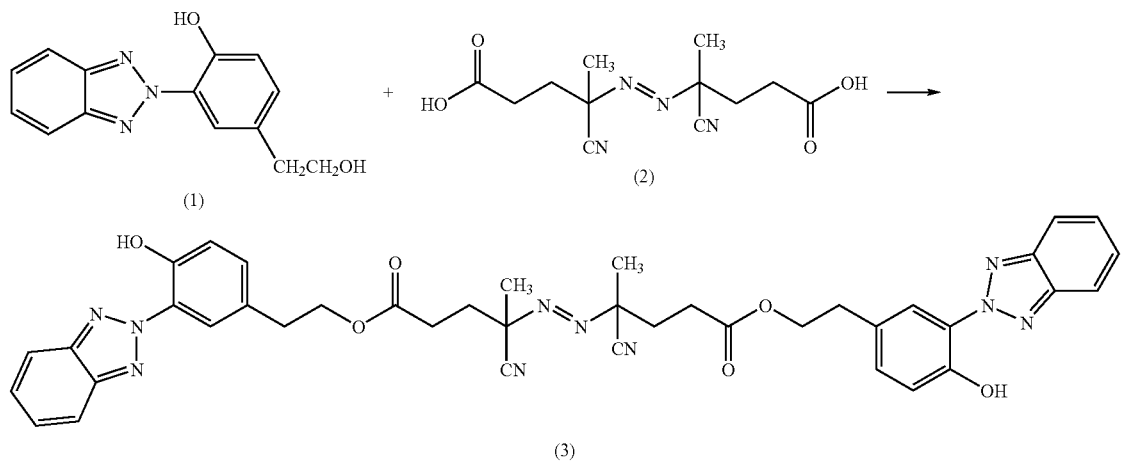

This invention provides the synthesis of a single component additive that provides a dual function: UV absorption properties and ability to initiate free radical polymerization. The result is a covalently linked UV absorber that will not leach out of the product or phase separate and lead to decreased optical clarity. The synthesis permits flexibility in tailoring both UV absorbing strength and initiator half-life. UV-initiation of polymerization of the lens material is still possible with protection of the hydroxy group on the UV absorbing function of the DFUVAS.

The DFUVAS can be synthesized from azo, organic peroxide, phosphine oxide, and α-hydroxyketone radical polymerization initiators that contain appropriate functional groups. The necessary functionality from each of these initiator classes is the presence of a functional group (carboxylic acid or hydroxyl) through which a UV absorbing benzotriazole, benzophenone or triazine can be covalently linked. Preferred DFUVAS are those represented by formulas [1]-[7].

Several functionalized azo initiators are commercially available. For example, V-501 (4,4'-azobis(4-cyanopentanoic acid)) from Wako Chemicals. This initiator contains a thermally labile azo linkage (—N=N—) and two terminal carboxylic acid groups. Similarly, VA-086 contains two terminal hydroxyl groups. VA-080 contains three hydroxyl groups on each side of the thermally labile azo linkage.

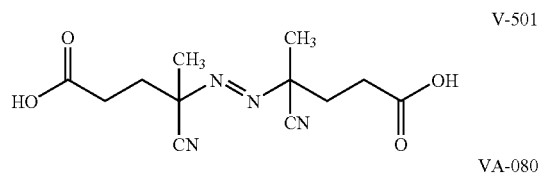

V-501

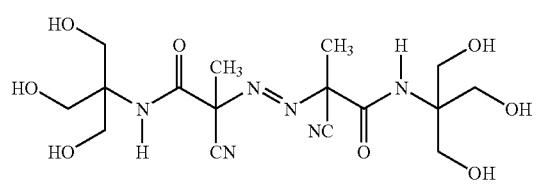

VA-080 where:

A is —CH$_3$ or —CH$_2$CH$_3$.

B is —CN, —CO$_2$H, —COH, —COCH$_3$, —CO$_2$CH$_3$, —SO$_3$H, —CF$_3$, or —NO$_2$ when D is (CH$_2$)$_n$, and —CH$_3$ or —CH$_2$CH$_3$ when D is nothing.

D is nothing or (CH$_2$)$_n$, n=1-10

E is O or NH, NCH$_3$, or NCH$_2$CH$_3$

F is nothing, (CH$_2$)$_x$ or (CH$_2$CH$_2$O)$_x$CH$_2$CH$_2$ where x=1-10.

G is —R, —OR, —NHR, —NRR', —CO$_2$R, or —COR, where R=a benzotriazole or benzophenone UV absorber, and R'=—CH$_3$ or —CH$_2$CH$_3$.

Many benzotriazole and benzophenone UV absorbers are known and many are commercially available from a variety of sources, such as Ciba Specialty Chemicals. The identity of the benzotriazole or benzophenone UV absorber is not critical, but should be selected based on its characteristic UV cut-off to give the desired UV absorbing property. For IOL applications, preferred benzotriazole UV absorbers are hydroxyphenylbenzotriazole and preferred benzophenone UV absorbers are hydroxyphenylbenzophenones that have been modified to contain a functional group that can be covalently bonded to a radical polymerization initiator. For example, a preferred hydroxyphenylbenzotriazole UV absorber is 2-N-(2-hydroxyphenyl)benzotriazole, where the UV absorbing group is linked through an ethyl ether linkage at the para position on the hydroxyphenyl group, as shown below linked to an azo functionality.

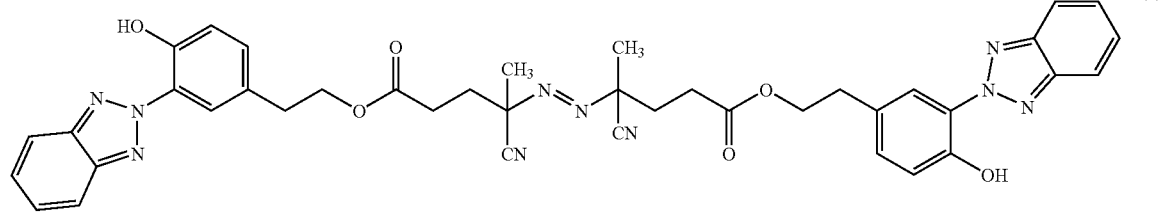

(3)

-continued

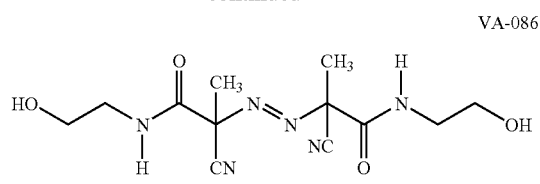

VA-086

Therefore, an azo functional UV absorber can be synthesized from an azo initiator with the following structural characteristics:

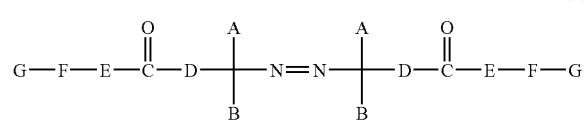

[1]

Functionalized α-hydroxyketones suitable for use as UV polymerization initiators are commercially available. For example, 2-hydroxy-1-[4-(2-hydroxy-ethoxy)phenyl]-2-methylpropan-1-one (Irgacure® 2959, Ciba Specialty Chemicals) contains a free primary hydroxyl group covalently attached to a UV light labile α-hydroxyketone linkage. This primary hydroxyl can be used as a covalent linking point. For example, in Irgacure® 2959, the primary hydroxyl was used to covalently attach hydrophilic functional groups through an ether linkage to create a water-soluble photoinitiator (Gruber, H. F.; Knaus, S. J. Polym. Sci. Part A: Polym. Chem. 1995, 33, 929).

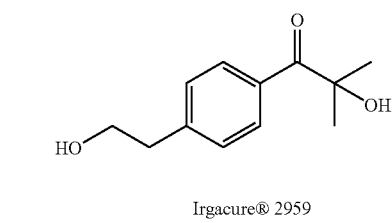

Irgacure® 2959

A generic α-hydroxyketone photoinitiator that contains the appropriate functional groups for covalently linking a UV chromophore is represented by formula [2]:

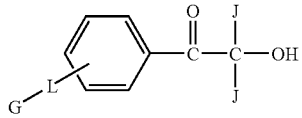

[2]

where:

J is CH₃ or CH₂CH₃.

L is nothing, $(CH_2)_y$, or $(CH_2CH_2O)_y$, where y=1-10.

G is —R, —OR, —NHR, —NRR', —CO₂R, or —COR, where R=a benzotriazole or benzophenone UV absorber, and R'=—CH₃ or —CH₂CH₃.

Functionalized phosphine oxide photoinitiators are also known. For example, a vinyl functional phosphine oxide was used in the synthesis of polymeric acylphosphine oxide photoinitiators (DeGroot, J. H.; Dillingham, K. A.; Deuring, H.; Haitjema, H. J.; Van Beijma, F. J.; Hodd, K. A.; Norrby, S. *Biomacromolecules* 2001, 2, 1271).

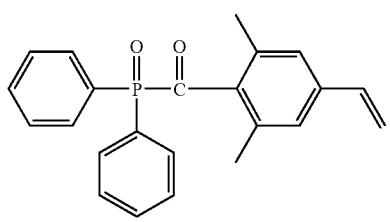

A generic phosphine oxide photoinitiator that contains the appropriate functional groups for covalently linking a UV chromophore is represented by formula [3].

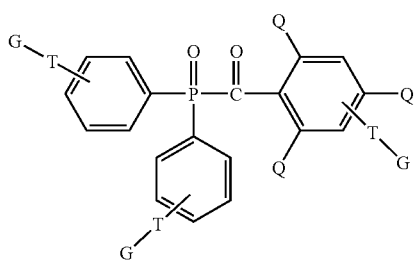

[3]

where Q is —H, —CH₃, —CH₂CH₃, —CH(CH₃)CH₃, or —C(CH₃)₃.

T is nothing, $(CH_2)_z$, or $(OCH_2CH_2)_z$, where z=1-10

G is —R, —OR, —NHR, —NRR', —CO₂R, or —COR, where R=a benzotriazole or benzophenone UV absorber, and R'=—CH₃ or —CH₂CH₃.

Functionalized organic peroxides are less common, however the presence of a functional group for example OH, NH₂, or CO₂H would allow covalent attachment of a benzotriazole- or benzophenone-containing UV chromophore. A generic acylperoxide initiator that contains appropriate functional groups for covalently linking a UV chromophore is represented by formula [4].

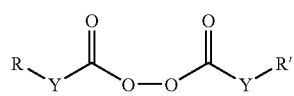

[4]

where Y=nothing or O; R=a benzotriazole or benzophenone UV absorber; R'=a benzotriazole or benzophenone UV absorber; —(CH₂)$_n$H (n=1-18); —CH(CH₃)CH₃; —C(CH₃)₃; —C₆H₅; —CH(CH₃)CH₂CH₃; —C(CH₃)₂CH₂C(CH₃)₃; —C(CH₃)₂(CH₂)₄H; —C(CH₂CH₃)₂(CH₂)₄H; —C(CH₃)₂(CH₂)₅H; —C(CH₂CH₃)₂(CH₂)₅H; —C(CH₃)₂(CH₂)₆H; —C(CH₂CH₃)₂(CH₂)₆H; —CH₂CH(CH₂CH₃)(CH₂O; or

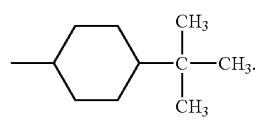

By way of illustration, if Y=O and R and R' in formula [4] are selected to be the benzotriazole UV absorber 2-N-(2-hydroxyphenyl)benzotriazole, and the UV absorbing group is linked through an ethyl linkage at the para position on the hydroxyphenyl group to the peroxydicarbonate functionality, the following compound is obtained:

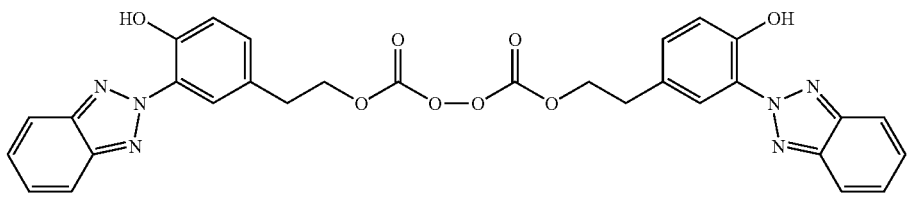

Generic peroxyester, dialkylperoxide and peroxyketal initiators that contain the appropriate functional groups for covalently linking a UV chromophore are represented by formulas [5], [6], and [7], respectively.

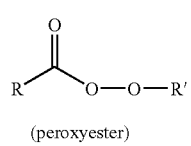

[5]

(peroxyester)

where R=a benzotriazole or benzophenone UV absorber; R'=a benzotriazole or benzophenone UV absorber; —(CH₂)$_n$H (n=1-18); —CH(CH₃)CH₃; —C(CH₃)₃;

—C$_6$H$_5$; —CH(CH$_3$)CH$_2$CH$_3$; —C(CH$_3$)$_2$CH$_2$C(CH$_3$)$_3$; —C(CH$_3$)$_2$(CH$_2$)$_4$H; —C(CH$_2$CH$_3$)$_2$(CH$_2$)$_4$H; —C(CH$_3$)$_2$(CH$_2$)$_5$H; —C(CH$_2$CH$_3$)$_2$(CH$_2$)$_5$H; —C(CH$_3$)$_2$(CH$_2$)$_6$H; —C(CH$_2$CH$_3$)$_2$(CH$_2$)$_6$H; —CH$_2$CH(CH$_2$CH$_3$)(CH$_2$)$_4$H; —C(CH$_3$)$_2$C$_6$H$_5$; or

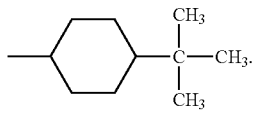

R—O—O—R(dialkylperoxide) [6]

where R=a benzotriazole or benzophenone UV absorber; R'=H, a benzotriazole or benzophenone UV absorber; —(CH$_2$)$_n$H (n=1-18); —CH(CH$_3$)CH$_3$; —C(CH$_3$)$_3$; —CH(CH$_3$)CH$_2$CH$_3$; —C(CH$_3$)$_2$CH$_2$C(CH$_3$)$_3$; —C(CH$_3$)$_2$(CH$_2$)$_4$H; —C(CH$_2$CH$_3$)$_2$(CH$_2$)$_4$H; —C(CH$_3$)$_2$(CH$_2$)$_5$H; —C(CH$_2$CH$_3$)$_2$(CH$_2$)$_5$H; —C(CH$_3$)$_2$(CH$_2$)$_6$H; —C(CH$_2$CH$_3$)$_2$(CH$_2$)$_6$H; —CH$_2$CH(CH$_2$CH$_3$)(CH$_2$)$_4$H; or —C(CH$_3$)$_2$C$_6$H$_5$.

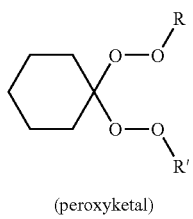

(peroxyketal)

where R=a benzotriazole or benzophenone UV absorber; R'=H; a benzotriazole or benzophenone UV absorber; (CH$_2$)$_n$H (n=1-18); CH(CH$_3$)CH$_3$; C(CH$_3$)$_3$; CH(CH$_3$)CH$_2$CH$_3$; C(CH$_3$)$_2$CH$_2$C(CH$_3$)$_3$; C(CH$_3$)$_2$(CH$_2$)$_4$H; C(CH$_2$CH$_3$)$_2$(CH$_2$)$_4$H; C(CH$_3$)$_2$(CH$_2$)$_5$H; C(CH$_2$CH$_3$)$_2$(CH$_2$)$_5$H; C(CH$_3$)$_2$(CH$_2$)$_6$H; C(CH$_2$CH$_3$)$_2$(CH$_2$)$_6$H; CH$_2$CH(CH$_2$CH$_3$)(CH$_2$)$_4$H; or C(CH$_3$)$_2$C$_6$H$_5$.

In general, the amount of DFUVAS contained in ophthalmic lens materials will depend upon the desired UV blocking characteristics but will typically range from 1-5 wt %.

The invention will be further illustrated by the following examples, which are intended to be illustrative, but not limiting.

Example 1

Esterification of 4,4'-azobis(4-cyanopentanoic acid) with 3-(2H-benzotriazol-2-yl)-4-hydroxyphenethyl alcohol A 50 mL 3-neck flask was dried in a 120° C. oven overnight and cooled in a desiccator. The flask flushed with N$_2$ then charged with 1.9151 g (7.50 mmol) of 3-(2H-benzotriazol-2-yl)-4-hydroxyphenethyl alcohol. The solid was dissolved in 15 mL anhydrous tetrahydrofuran, then 4-dimethylaminopyridine (0.0489 g, 0.400 mmol) and 4,4'-azobis(4-cyanopentanoic acid) (1.0084 g, 3.60 mmol), were added and allowed to dissolve. 1,3-Dicyclohexyl carbodiimide (1.5520 g, 7.52 mmol) was added and the reaction mixture was allowed to stir at ambient temperature under a N$_2$ blanket for 24 hr. The reaction mixture was filtered through a fine porosity sintered glass funnel and the solvent was rotovapped. The crude product was purified by column chromatography (silica gel, CH$_2$Cl$_2$), the solvent was rotovapped and the product was dried under vacuum. Yield 1.3691 g (1.81 mmol, 51%) of a pale yellow powder.

Example 2

Preparation of Ophthalmic Lens Material Initiated with UV Absorbing Initiator Prepared in Example 1

A scintillation vial was charged with 3.3572 g (19.052 mmol) of 2-phenylethyl acrylate (PEA), 1.5585 g (8.192 mmol) of 2-phenylethyl methacrylate (PEMA), and 0.0611 g (0.308 mmol) of 1,4-butanediol diacrylate (BDDA). The monomer mixture was purged with N$_2$ and 0.2290 g (0.304 mmol) of the UV absorbing initiator prepared in Example 1 was added and allowed to dissolve. The initiated formulation was filtered through a 0.2 micron PTFE filter and dispensed into polypropylene molds. The molds were placed in an oven for 1 hr at 70° C. then 2 hrs at 110° C. The product polymer was extracted in acetone at room temperature for 16 hrs. The polymer was allowed to air dry for 1.5 hr, then placed in a 60° C. vacuum oven for 3 hrs. The weight loss following extraction was determined gravimetrically and the UV/Vis spectrum was recorded from 190 to 820 nm on a 1 mm thick flat. The data is listed in Table 1.

Example 3

Preparation of Ophthalmic Lens Material Initiated with UV Absorbing Initiator Prepared in Example 1

A scintillation vial was charged with 3.3502 g (19.012 mmol) of 2-phenylethyl acrylate (PEA), 1.5516 g (8.156 mmol) of 2-phenylethyl methacrylate (PEMA), and 0.0567 g (0.286 mmol) of 1,4-butanediol diacrylate (BDDA). The monomer mixture was purged with N$_2$ and 0.0761 g (0.101 mmol) of the UV absorbing initiator prepared in Example 1 was added and allowed to dissolve. The initiated formulation was filtered through a 0.2 micron PTFE filter and dispensed into polypropylene molds. The molds were placed in an oven for 1 hr at 70° C. then 2 hrs at 110° C. The product polymer was extracted in acetone at room temperature for 16 hrs. The polymer was allowed to air dry for 1.5 hr, then placed in a 60° C. vacuum oven for 3 hrs. The weight loss following extraction was determined gravimetrically and the UV/Vis spectrum was recorded from 190 to 820 nm on a 1 mm thick flat. The data is listed in Table 1.

Example 4

Preparation of Ophthalmic Lens Material Initiated with 2,2'-azobisisobutyronitrile (AIBN)

A scintillation vial was charged with 3.3580 g (19.057 mmol) of 2-phenylethyl acrylate (PEA), 1.5629 g (8.215 mmol) of 2-phenylethyl methacrylate (PEMA), and 0.0589 g (0.297 mmol) of 1,4-butanediol diacrylate (BDDA). The monomer mixture was purged with N$_2$ and 0.0502 g (0.306 mmol) of 2,2'-azobisisobutyronitrile (AIBN) was added and allowed to dissolve. The initiated formulation was filtered through a 0.2 micron PTFE filter and dispensed into polypropylene molds. The molds were placed in an oven for 1 hr at 70° C. then 2 hrs at 110° C. The product polymer was extracted in acetone at room temperature for 16 hrs. The polymer was allowed to air dry for 1.5 hr, then placed in a 60° C. vacuum oven for 3 hrs. The weight loss following extraction was determined gravimetrically and the UV/Vis spectrum was recorded from 190 to 820 nm on 1 mm thick flat. The data is listed in Table 1.

TABLE 1

| | Weight % acetone extractables and UV cut-off of ophthalmic lens materials. | | |
|---|---|---|---|
| Example | % extractables | 10% T (nm) | 1% T (nm) |
| 2 | 3.86 ± 0.18 | 381 | 377 |
| 3 | 4.82 ± 0.25 | 377 | 371 |
| 4 | 0.63 ± 0.23 | 294 | 279 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

I claim:

1. A dual function UV absorber of the formula:

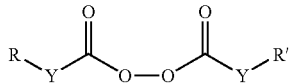

[4]

where Y=nothing or O; R=a benzotriazole or benzophenone UV absorber; R'=a benzotriazole or benzophenone UV absorber; —(CH$_2$)$_n$H (n=1-18); —CH(CH$_3$)CH$_3$; —C(CH$_3$)$_3$; —C$_6$H$_5$; —CH(CH$_3$)CH$_2$CH$_3$; —C(CH$_3$)$_2$CH$_2$C(CH$_3$)$_3$; —C(CH$_3$)$_2$(CH$_2$)$_4$H; —C(CH$_2$CH$_3$)$_2$(CH$_2$)$_4$H; —C(CH$_3$)$_2$(CH$_2$)$_5$H; —C(CH$_2$CH$_3$)$_2$(CH$_2$)$_5$H; —C(CH$_3$)$_2$(CH$_2$)$_6$H; —C(CH$_2$CH$_3$)$_2$(CH$_2$)$_6$H; —CH$_2$CH(CH$_2$CH$_3$)(CH$_2$)$_4$H; or

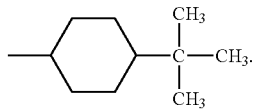

2. A dual function UV absorber of the formula:

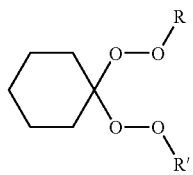

[7]

where R=a benzotriazole or benzophenone UV absorber; R'=H; a benzotriazole or benzophenone UV absorber; (CH$_2$)$_n$H (n=1-18); CH(CH$_3$)CH$_3$; C(CH$_3$)$_3$; CH(CH$_3$)CH$_2$CH$_3$; C(CH$_3$)$_2$CH$_2$C(CH$_3$)$_3$; C(CH$_3$)$_2$(CH$_2$)$_4$H; C(CH$_2$CH$_3$)$_2$(CH$_2$)$_4$H; C(CH$_3$)$_2$(CH$_2$)$_5$H; C(CH$_2$CH$_3$)$_2$(CH$_2$)$_5$H; C(CH$_3$)$_2$(CH$_2$)$_6$H; C(CH$_2$CH$_3$)$_2$(CH$_2$)$_6$H; CH$_2$CH(CH$_2$CH$_3$)(CH$_2$)$_4$H; or C(CH$_3$)$_2$C$_6$H$_5$.

3. An ophthalmic lens material comprising a dual function UV absorber of claim 1.

4. The ophthalmic lens material of claim 3 wherein the dual function UV absorber is present in the ophthalmic lens material in an amount of 1-5% (w/w).

5. An ophthalmic lens material comprising a dual function UV absorber of claim 2.

6. The ophthalmic lens material of claim 5 wherein the dual function UV absorber is present in the ophthalmic lens material in an amount of 1-5% (w/w).

* * * * *